US00PP37621P2

(12) United States Plant Patent
Ho

(10) Patent No.: US PP37,621 P2
(45) Date of Patent: Aug. 18, 2026

(54) ***SCHISMATOGLOTTIS* PLANT NAMED 'RPFSTRDST'**

(50) Latin Name: ***Schismatoglottis* sp.**
Varietal Denomination: RPFSTRDST

(71) Applicant: RARE PLANT FAIRY, LLC, Detroit, MI (US)

(72) Inventor: Jocelyn Ho, Detroit, MI (US)

(73) Assignee: Rare Plant Fairy, LLC, Detroit, MI (US)

( * ) Notice: Subject to any disclaimer, the term of this patent is extended or adjusted under 35 U.S.C. 154(b) by 0 days.

(21) Appl. No.: 19/357,256

(22) Filed: Oct. 14, 2025

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

PUBLICATIONS

Facebook 2024, Pandawa Plants, retrieved online at https://www.facebook.com/pandawaplants/videos/938204324499798/, 3 pp. (Year: 2024).*
Hay, The genus Schismatoglottis Zoll. & Moritzi (Araceae : Schismatoglottideae) in Peninsular Malaysia and Singapore, Sandakania 7 (1996): 1-7 (Year: 1996).*
Instagram 2025, Rare Plant Fairy, retrieved online at https://www.instagram.com/p/DGBGps8Oyiu/?hl=en&img_index=2, 2 pp. (Year: 2025).*

* cited by examiner

*Primary Examiner* — June Hwu
(74) *Attorney, Agent, or Firm* — James R. Holm; Plant Novelty Rights, LLC

(57) ABSTRACT

A new and distinct *Schismatoglottis* plant named 'RPFSTRDST' particularly distinguished by unique, fine marbled, speckled, and streaked leaf variegation pattern evenly distributed over the entire lamina resembling a starry sky; stable leaf variegation that does not revert to solid green under low light conditions; compact, clumping growth habit with short internodes, suitable for growing in containers; and foliage that maintains high ornamental value year-round.

5 Drawing Sheets

Figure 1:
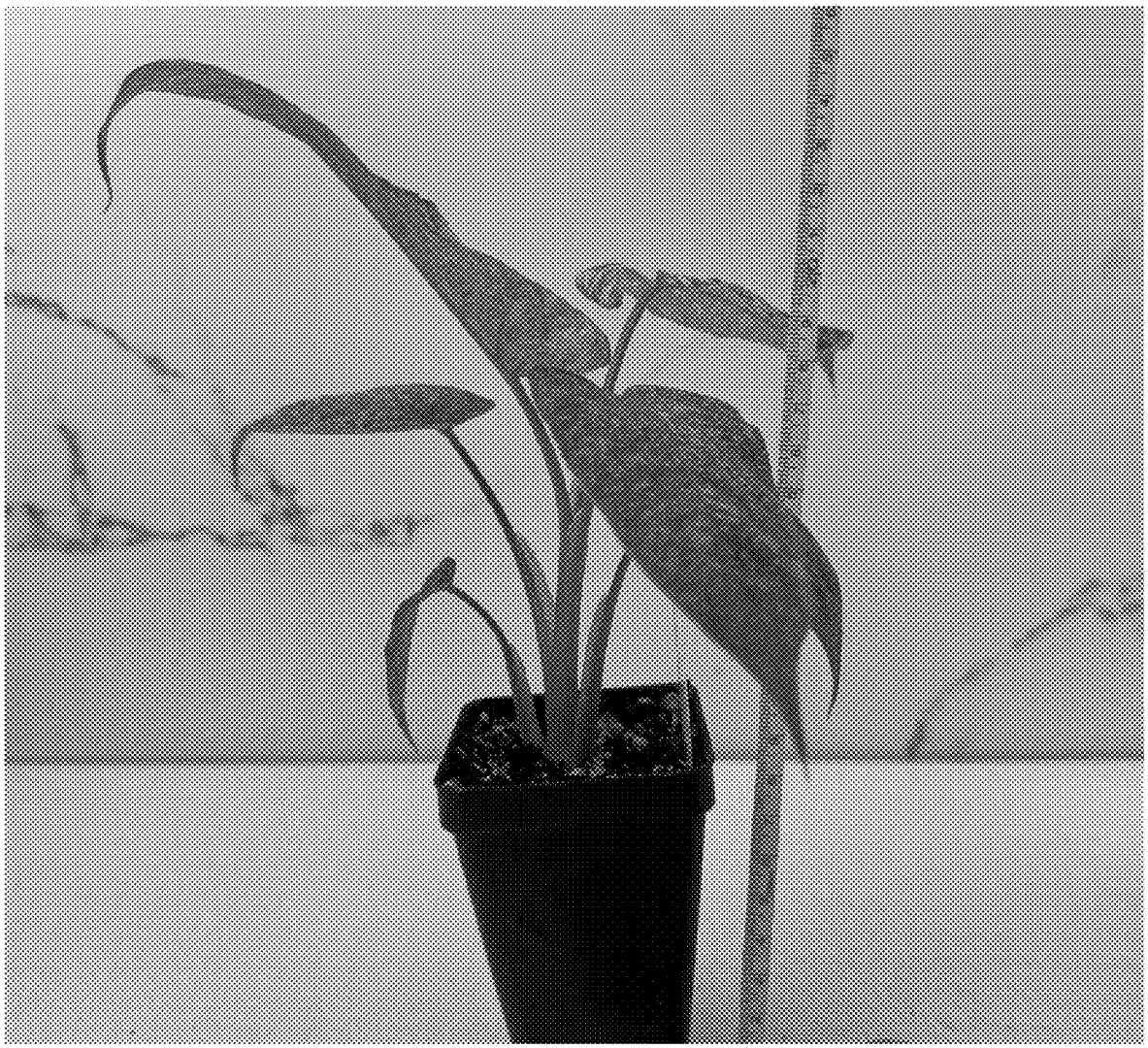

Genus and species: *Schismatoglottis* sp.
Variety denomination: 'RPFSTRDST'.

STATEMENT REGARDING PRIOR DISCLOSURES BY THE INVENTOR

The inventor asserts that no publications or advertisements relating to sales, offers for sale, or public distribution occurred more than one year prior to the effective filing date of this application. Any information about the claimed plant would have been obtained from a direct or indirect disclosure from the inventor. The inventor claims a prior art exemption under 35 U.S.C. 102(b)(1) for disclosures and/or sales that fall within a one-year grace period prior to the effective filing date of this application. Plants of 'RPFSTRDST' have been or will be sold under the commercial trademark "Fairy's Stardust".

BACKGROUND OF THE NEW PLANT

The present invention comprises a new and distinct variety of *Schismatoglottis* plant, botanically known as *Schismatoglottis* sp., and hereinafter referred to by its name 'RPFSTRDST'.

The new *Schismatoglottis* cultivar originated as a naturally occurring, single plant mutation within a population of unnamed and unpatented plants of *Schismatoglottis* sp. The new *Schismatoglottis* cultivar was discovered in June 2024 by the inventor in a controlled environment facility located in Detroit, Michigan. The new cultivar was selected for further asexual propagation and commercialization due to its unique and distinctive speckled variegated foliage. Asexual reproduction of 'RPFSTRDST' by rhizome divisions was first performed in September 2024 in Detroit, Michigan and has shown that the unique features of this new *Schismatoglottis* cultivar are stable and reproduced true-to-type through 3 successive generations of asexual reproduction.

SUMMARY OF THE INVENTION

The new *Schismatoglottis* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Schismatoglottis* cultivar. The combination of these characteristics distinguishes 'RPFSTRDST' as a new and distinct variety of *Schismatoglottis:*

1. Unique, fine marbled, speckled, and streaked leaf variegation pattern evenly distributed over the entire lamina resembling a starry sky;
2. Stable leaf variegation that does not revert to solid green under low light conditions;
3. Compact, clumping growth habit with short internodes, suitable for growing in containers; and 4. Foliage that maintains high ornamental value year-round.

Plants of 'RPFSTRDST' can be compared to plants of the parent or progenitor, *Schismatoglottis* sp. However, 'RPFSTRDST' differs in the following characteristics:

1. 'RPFSTRDST' has dense, fine specked leaf variegation pattern colored pale yellow-green to chartreuse uniformly distributed across the entire leaf surface, whereas the parent or progenitor plants have uniform, solid medium green leaf coloration with no variegation; and
2. 'RPFSTRDST' has a more compact and clumping growth habit, shorter internodes, and a smaller overall plant height compared to plants of the parent or progenitor.

Plants of 'RPFSTRDST' can be compared to the commercial *Schismatoglottis wallichii* cultivar 'Sarawak' (unpatented). However, the new *Schismatoglottis* cultivar 'RPFSTRDST' differs from plants of 'Sarawak' in the following characteristic:

1. 'RPFSTRDST' has dense, fine specked leaf variegation pattern colored pale yellow-green to chartreuse uniformly distributed across the entire leaf surface, whereas 'Sarawak' has irregular blocks or brush-stroke patterns of lighter green or cream leaf variegation, often asymmetrical and concentrated along the midrib and margins with large solid green areas remaining.

DESCRIPTION OF THE PHOTOGRAPHS

This new *Schismatoglottis* cultivar is illustrated by the accompanying-colored photographs which show the overall appearance and distinct characteristics of the plant. The colors shown are as true as can be reasonably obtained by conventional photographic procedures. The photographs were taken in July 2025 and represent 9-month-old plants grown in 2.5-inch by 2.5-inch containers under artificial light in a controlled environment facility in Detroit, Michigan. Colors in the photographs may differ slightly from the color values cited in the botanical description which accurately describes the colors of the new variety.

FIG. 1. shows a side view of the overall plant form and foliage of 'RPFSTRDST'.

Figure 2:
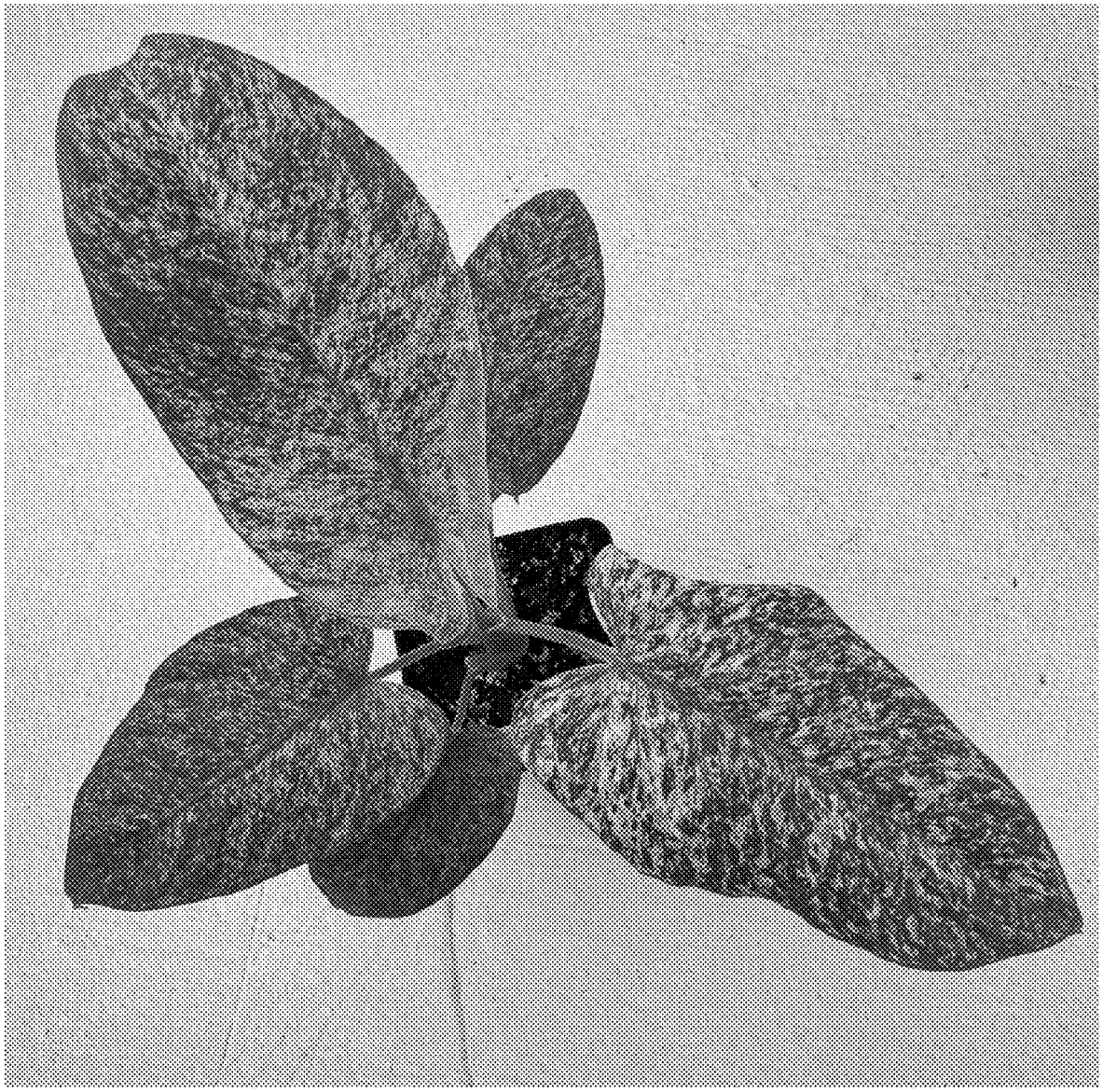

FIG. 2. shows an overhead view of the overall plant form and foliage of 'RPFSTRDST'.

Figure 3:
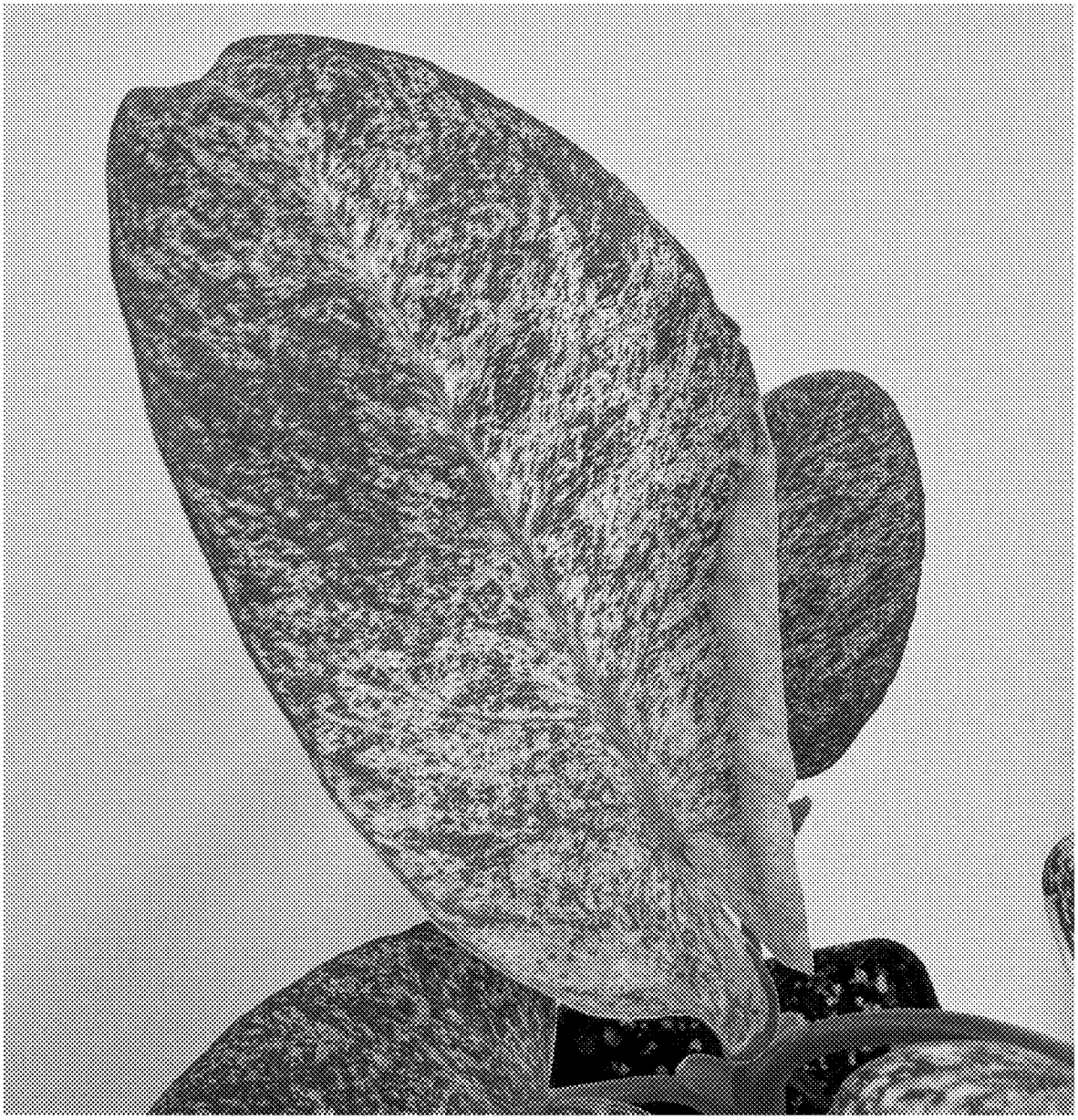

FIG. 3. shows a closeup view of the adaxial surface of a typical newly emerged leaf of 'RPFSTRDST'.

Figure 4:
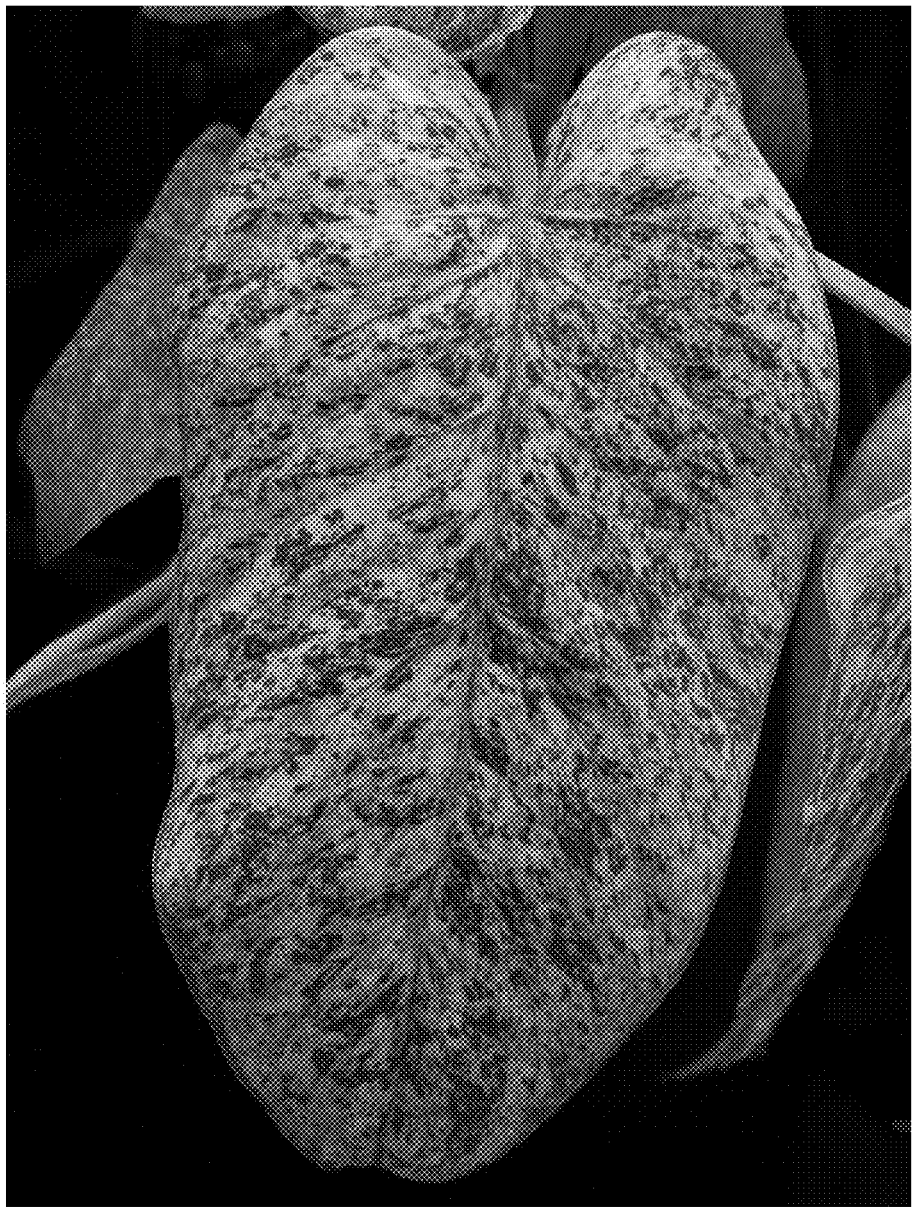

FIG. 4. shows a closeup view of the adaxial surface of a typical mature leaf of 'RPFSTRDST'.

Figure 5:
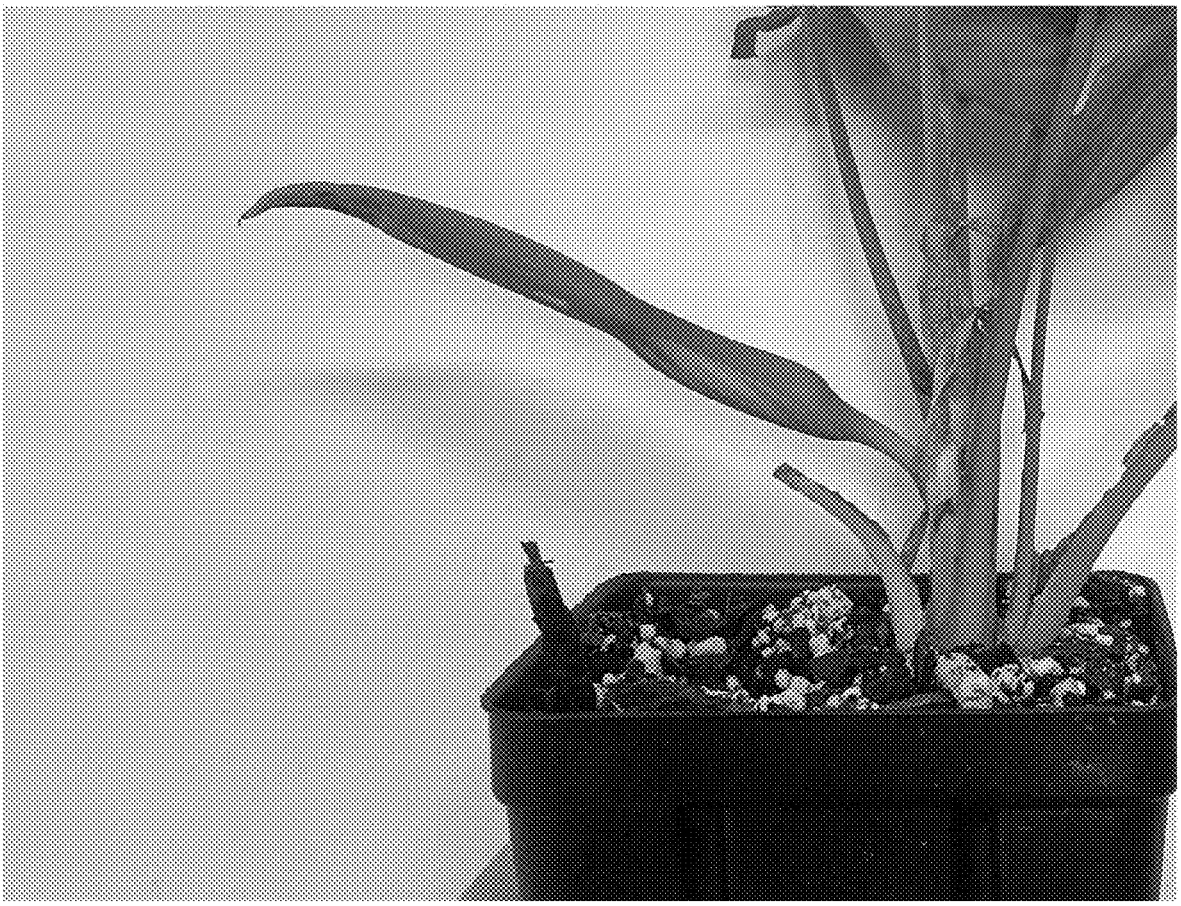

FIG. 5. shows a closeup of a typical inflorescence observed on plants of 'RPFSTRDST'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a controlled environment facility in Detroit, Michigan with an average temperature of 75 degrees Fahrenheit and 68 percent humidity. Detailed descriptions were taken in August 2025 from 10-month-old plants grown in 2.5-inch by 2.5-inch containers. Measurements and numerical values represent averages of typical plant types.

DETAILED BOTANICAL DESCRIPTION

Classification:

*Family*.—Araceae.

*Botanical*.—*Schismatoglottis* sp.

*Common*.—*Schismatoglottis*.

*Denomination*.—'RPFSTRDST'.

General description:

*Plant type*.—Rhizomatous, tropical evergreen perennial.

*Growth habit*.—Upright and outwardly arching.

*Height from soil level to top of foliar plane*.—Approximately 12.0 cm.

*Plant spread*.—Approximately 28.0 cm to 30.0 cm.

*Primary stem*.—Rhizomatous, approximately 1.0 cm in diameter at the base.

*Number of young axillary stems per primary stem*.—4 to 5.

*Primary and young axillary stem color*.—150C to 150D (yellow green); stems are generally not visible as the petiole wings clasp the stem.

*Internode length*.—Approximately 1.0 cm.

*Growth rate*.—Moderate, 1 to 2 leaves emerging per month per active meristem.

*Propagation type*.—Rhizome divisions.

*Time to initiate roots*.—Adventitious roots initiate approximately 7 to 14 days after division.

*Time to produce a rooted cutting*.—Approximately 3 to 6 weeks.

*Roots*.—Fibrous to semi-fleshy, arising from a short, condensed rhizome at the plant's base, approximately 1.0 mm to 2.0 mm in diameter, smooth, and glabrous; colored creamy white to light tan when fresh, occasionally developing light brown sheathing with age; capable of forming both below the soil surface and along buried portions of the stem, contributing to strong anchorage and rapid establishment after propagation.

Foliage description:

*Quantity of leaves per stem*.—Primary stems: Approximately 6. Young axillary stems: 2 to 3.

*Arrangement*.—Alternate.

*Attachment*.—Petiolate.

*Lamina*.—Shape: Ovate. Length: Approximately 14.5 cm. Width: Approximately 6.0 cm at the widest point above the base of the lamina. Orientation: Upwards and slightly angled on newly emerged leaves, becoming horizontal as leaves mature and then pendulous at later stages of development of mature leaves. Apex: Acuminate and drooping. Base: Lobate, lobes are about 1.5 cm in length and about 2.0 cm in width when measured at the narrowest point of the sinus out to the leaf margin; sinus opening is about 2.0 cm in width at the base of the lobes. Margins: Entire, slightly undulating. Texture and luster, adaxial surface: Glabrous and weakly bullate between impressed primary veins; overall satin in luster with more sheen on the mid rib, no pubescence. Texture and luster, abaxial surface: Glabrous and slightly glaucescent; matte in luster; veins raised; thin-membranous feel; fine reticulation visible; no pubescence. Midrib: Slightly recessed on the upper surface and protruding on the lower surface. Venation pattern: Pinnate; recessed on the upper surface and protruding on the lower surface. Color: Newly emerged foliage, adaxial surface: A fine marbled, speckled and streaked mixture of 193A to 193C (pale yellow green), 155C (greenish white) with slight tints of 150C (brilliant yellow green) and a background coloration of 137C (moderate yellow green) and 139A (dark yellowish green); the darker yellow-green colorations appear more concentrated in the upper half of the lamina, whereas the lighter yellow-green colorations appear more concentrated in the lower half of the lamina. Primary vein and secondary veins: A marbled mixture of 150C (brilliant yellow green) and 143C (strong yellow green). Newly emerged foliage, abaxial surface: A marbled and streaked mixture of 155A (pale yellow green), 138A to 138B (moderate yellowish green), 190C to 190D (pale green); the darker yellow-green colorations appear more concentrated in the upper half of the lamina, whereas the lighter yellow-green colorations appear more concentrated in the lower half of the lamina. Primary vein: 145B (light yellow green). Secondary veins: 145B (light yellow green), near the primary vein, and 137A (moderate olive green) towards the leaf margin. Mature foliage, adaxial surface: A fine marbled, speckled and streaked mixture of 138A (moderate yellowish green), 191C to 191D (light grey), and 155C (greenish white) with a background coloration of 139A (dark yellowish green); the darker yellow-green colorations appear more concentrated in the upper two-thirds portion of the lamina, whereas the lighter yellow-green colorations appear more concentrated in the lower one-third portion of the lamina. Primary vein and secondary veins: A marbled mixture of 138A (moderate yellowish green) and 144A (strong yellow green). Mature foliage, abaxial surface: An evenly distributed, marbled mixture of 191C to 191D (light grey), 155A (pale yellow green), and 145B to 145C (light yellow green). Primary vein: 145A (strong yellow green). Secondary veins: 137C (moderate yellow green).

*Petioles*.—Shape: Rounded on the underside and trough-shape on the upper side. Aspect: Arching. Length: Approximately 3.5 cm to 4.0 cm from the apex of the petiole wing to the point of attachment to the lamina. Width: Approximately 0.2 cm at the point of attachment to the lamina and gradually widening to 0.3 cm at the apex of the petiole wing. Texture and luster: Glabrous, smooth to faintly longitudinally striate; satin (semi-gloss) in luster; sheath membranous, matte to weak satin in luster. Color (including outer surface of the wing): 145A (strong yellow green) near the attachment to the lamina then gradually darkening to 143B (strong yellow green) to the apex of the petiole wing and then lightening again to 145A through the center to the main stem. Wing length: Approximately 3.5 cm. Wing width (widest area at the base): Approximately 0.8 cm. Wing color (inner surface): A very translucent 157A to 157C (pale yellow green) and 145A with specks of 137D (moderate yellowish green).

Inflorescence description: Solitary to several together; peduncle 3.5 cm in length, generally shorter than the petioles, peduncle colored 145A (strong yellow green); spathe 9 to 11 cm in length with a lower tubular portion persistent and enveloping the pistillate zone, spathe colored 143B (strong yellow green); spathe limb (blade) caducous, shedding at or shortly after onset of staminate anthesis.

Fruit: No fruit observed to date.

Cold tolerance: Not cold tolerant.

Disease and pest tolerance: None observed.

Drought tolerance: None observed.

What is claimed is:

1. A new and distinct variety of *Schismatoglottis* plant named 'RPFSTRDST', substantially as illustrated and described herein.

* * * * *